United States Patent
Cook et al.

(10) Patent No.: US 8,327,685 B2
(45) Date of Patent: Dec. 11, 2012

(54) PARTICULATE MATTER SENSOR

(75) Inventors: James D. Cook, Freeport, IL (US);
Steven J. Magee, Lena, IL (US)

(73) Assignee: Honeywell International Inc.,
Morristown, NJ (US)

( * ) Notice: Subject to any disclaimer, the term of this patent is extended or adjusted under 35 U.S.C. 154(b) by 156 days.

(21) Appl. No.: 12/892,585

(22) Filed: Sep. 28, 2010

(65) Prior Publication Data

US 2012/0073267 A1 Mar. 29, 2012

(51) Int. Cl.
*G01M 15/10* (2006.01)
(52) U.S. Cl. ...................... 73/23.31; 73/23.33
(58) Field of Classification Search ............ 73/23.31, 73/23.33, 114.71
See application file for complete search history.

(56) References Cited

U.S. PATENT DOCUMENTS

| | | | |
|---|---|---|---|
| 6,634,210 B1 * | 10/2003 | Bosch et al. | 73/23.33 |
| 7,574,895 B2 * | 8/2009 | Schnell et al. | 73/28.01 |
| 7,770,432 B2 * | 8/2010 | Roesch et al. | 73/23.33 |
| 7,891,232 B2 * | 2/2011 | Hall | 73/28.01 |
| 7,954,230 B2 * | 6/2011 | Nelson | 29/612 |
| 8,030,086 B2 * | 10/2011 | Schmidt et al. | 436/155 |
| 2007/0119233 A1 * | 5/2007 | Schnell et al. | 73/28.01 |
| 2007/0264158 A1 * | 11/2007 | Schmidt et al. | 422/94 |
| 2008/0264146 A1 * | 10/2008 | Roesch et al. | 73/23.33 |
| 2010/0229724 A1 * | 9/2010 | Tokuda et al. | 96/19 |

* cited by examiner

*Primary Examiner* — Freddie Kirkland, III
(74) *Attorney, Agent, or Firm* — Schwegman Lundberg & Woessner, P.A.

(57) ABSTRACT

A particulate matter sensor includes a ceramic rod, a first metal layer deposited on the ceramic rod, a ceramic layer deposited on the first metal layer, and a second metal layer deposited on the ceramic layer. The first metal layer serves as a source electrode, and the second metal layer serves as a detection electrode. In another embodiment, a particulate matter sensor includes a metal rod, a ceramic sheet deposited or wrapped around the ceramic rod, and a metal layer deposited on the ceramic layer or sheet. The metal rod serves as a source electrode, and the second metal layer serves as a detection electrode.

18 Claims, 4 Drawing Sheets

PARTICULATE MATTER SENSOR

TECHNICAL FIELD

The present disclosure relates to particulate matter sensors, and in an embodiment, but not by way of limitation, a particulate matter sensor using a metalized ceramic probe with metal and ceramic layers deposited thereon, and a particulate matter sensor using a metal probe with ceramic and metal layers deposited thereon.

BACKGROUND

Particulate matter sensors have several applications in many different industries. For example, a particulate matter sensor can be placed in the exhaust stream of a diesel engine, where it senses incomplete burn of the diesel fuel. When used in a diesel engine, it can be placed before or after any diesel particulate filter (DPF) that is used in connection with the diesel engine. When used in connection with diesel engines, sensor probes must maintain their sensitivity over a broad temperature range, and they must be robust in relation to fuel quality variation and fuel additives.

DETAILED DESCRIPTION

One or more embodiments use metalized ceramic technology as a probe in a particulate matter sensor. In an embodiment used on a diesel engine, a particulate matter sensor uses a ceramic coating or layer to sense charge variations in an exhaust stream of the engine. While the sensitivity to charge variations is primarily a function of the thickness, porosity, roughness, and density of the ceramic coating or layer, other material properties could also affect the sensitivity to charge variations. In an embodiment, the sensor has a center electrode that provides an electrical contact to a ceramic coating or layer in the probe. The sensor probe can be manufactured as a monolithic structure using metalized ceramic technology such as low or high temperature co-fired ceramic process technology. The resulting probe would then have metallization layers and dielectric (ceramic) layers deposited on the probe to form the sensor.

An embodiment of a metalized ceramic probe is manufactured using green (soft, unfired) ceramic in sheet form. A conductor, such as tungsten, is formed (printed) on the ceramic sheet. The sheet is then formed or rolled into a cylindrical shape. The upper area of the metalized ceramic probe can be brazed to a spark plug style connector by using a copper-silver (CuAg) braze alloy, or other brazing processes and alloys known to those of skill in the art.

Figure 1:
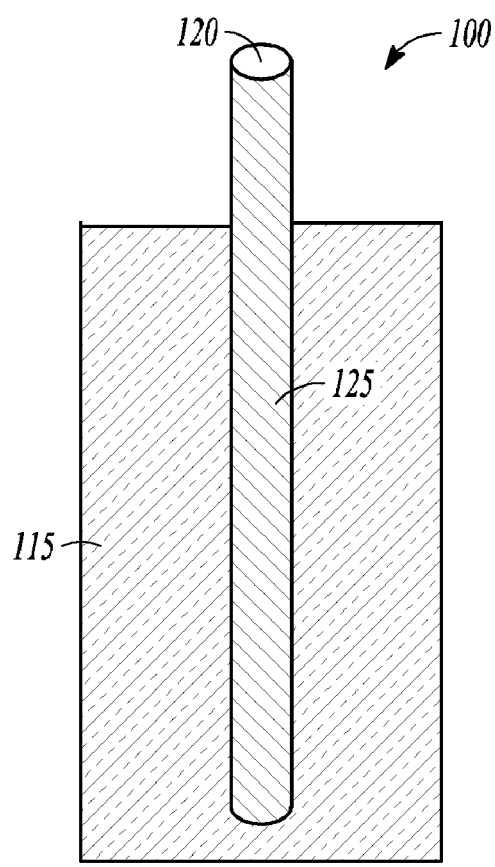
FIG. 1 illustrates an example embodiment of a multi-layer ceramic style particulate matter sensor probe.

FIG. 1 illustrates an example embodiment of a particulate matter sensor with a metalized ceramic probe. FIG. 1 shows sensor 100 that includes a ceramic layer or sheet 115. A ceramic rod 120 is provided, which is coated with a metal layer 125. The green ceramic sheet 115 is wrapped around the metalized ceramic rod 120 into a cylindrical shape. After forming the cylindrical shape, the ceramic sheet 115 and the metalized ceramic rod 120 are co-fired to form the sensor.

Figure 2:
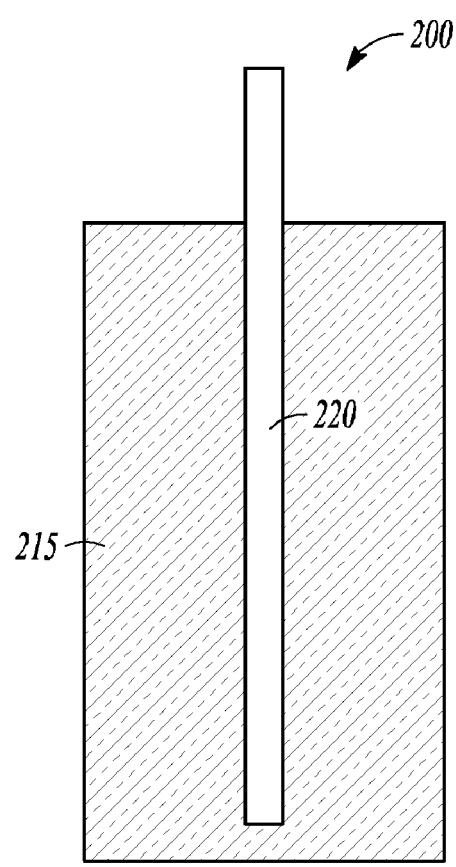
FIG. 2 illustrates another example embodiment of a multi-layer metal rod style particulate matter sensor probe.

FIG. 2 illustrates another example embodiment of a particulate matter sensor 200. The sensor 200 includes a ceramic layer or sheet 215. A metal rod conductor 220 (such as tungsten) is placed on the sheet 215. The ceramic layer or sheet 215 can then be deposited or rolled up into a cylinder to form the sensor.

Figures 3, 4:
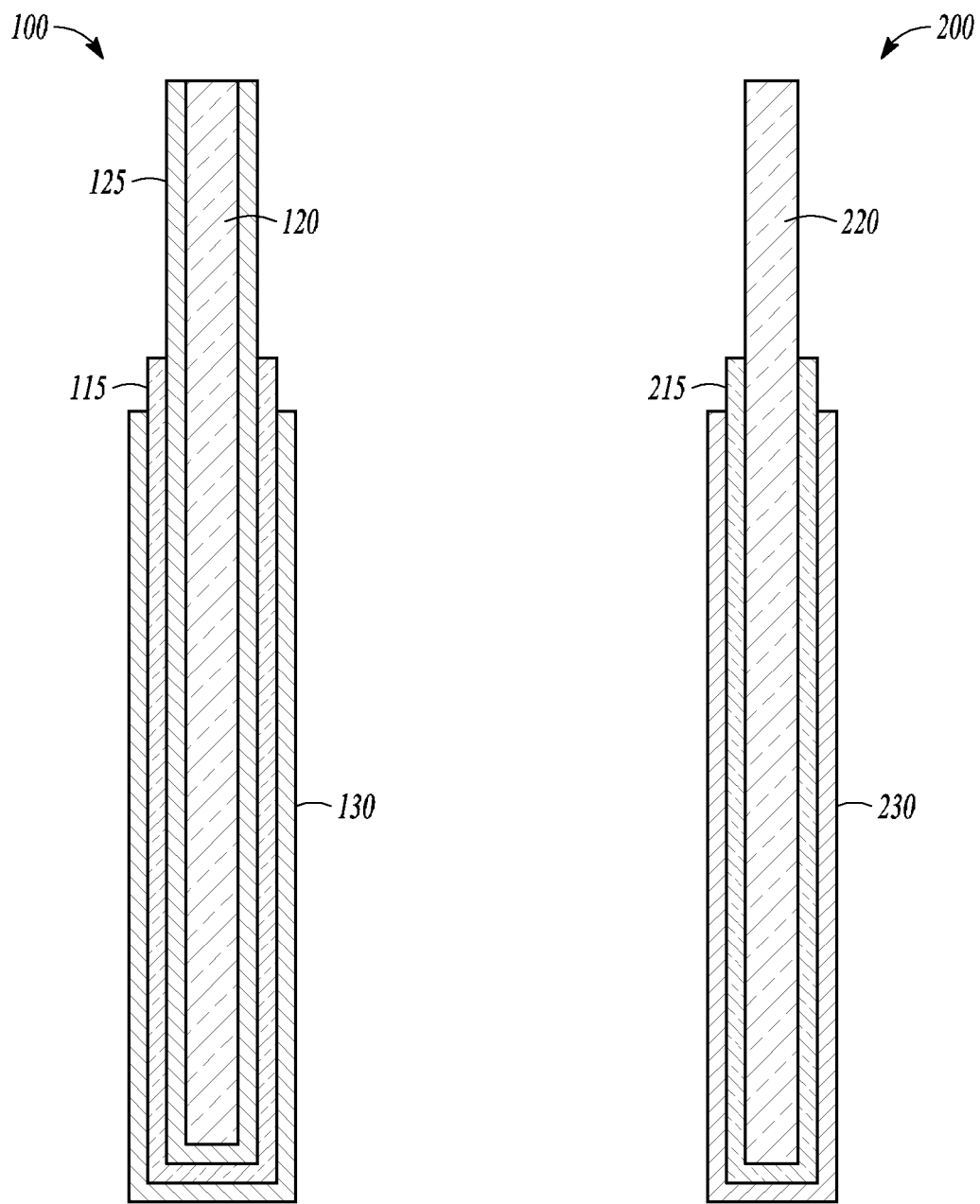
FIG. 3 illustrates the example embodiment of the multi-layer ceramic style particulate matter sensor probe of FIG. 1 in an assembled format.
FIG. 4 illustrates the example embodiment of the multi-layer metal rod style particulate matter sensor probe of FIG. 2 in an assembled format.

FIG. 3 illustrates the example embodiment of the multi-layer ceramic particulate matter sensor probe 100 of FIG. 1 in an assembled format. In the embodiment of FIG. 3, an aluminum oxide ceramic rod 120 is coated with a metal layer 125. The metal layer 125 serves as a source electrode. An aluminum oxide ceramic coating 115 is placed onto the metal layer 125, and another metal layer 130 is placed onto the ceramic layer 115. The metal layer 130 serves as a detection electrode.

FIG. 4 illustrates the example embodiment of the multi-layer ceramic particulate matter sensor probe 200 of FIG. 2 in an assembled format. The sensor 200 includes the metal rod conductor 220 (which serves as the source electrode), the ceramic layer or sheet 215 that is deposited on or wrapped around the metal rod conductor 220, and a metal layer 230 (which serves as the detection electrode).

Figure 5:
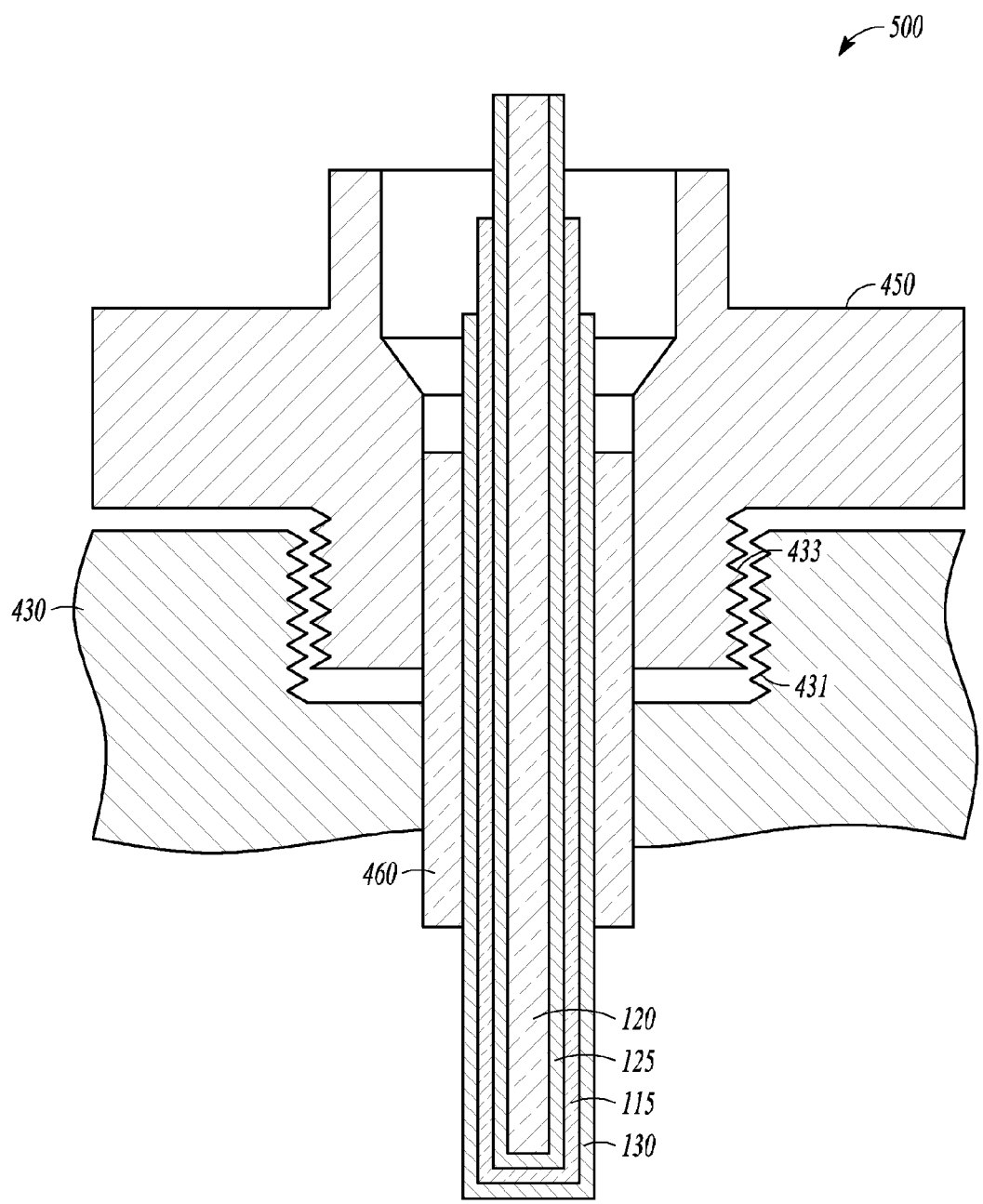
FIG. 5 illustrates the example embodiment of a multi-layer ceramic particulate matter sensor probe 100 of FIG. 3 installed in an engine block.

FIG. 5 illustrates an example embodiment 500 of the multi-layer ceramic particulate matter sensor probe 100 of FIG. 3 installed in an engine block 430. While sensor 100 is illustrated in FIG. 5, any of the disclosed sensor embodiments can be installed into the engine block. As illustrated in FIG. 5, the sensor 100 includes the aluminum oxide ceramic rod 120 that is coated with the metal layer 125. As noted above, the metal layer 125 serves as a source electrode. The aluminum oxide ceramic coating 115 is placed onto the metal layer 125, and the second metal layer 130 is placed onto the ceramic layer 115. As noted above, the metal layer 130 serves as a detection electrode. The sensor 100 in FIG. 5 also includes an insulator 460, which in an embodiment, is a glass insulator. As can be seen in FIG. 5, the sensor system 500 is installed into an engine block 430 via interlocking threads 431 and 433, and further held in place by a fitting or collar 450.

Figure 6:
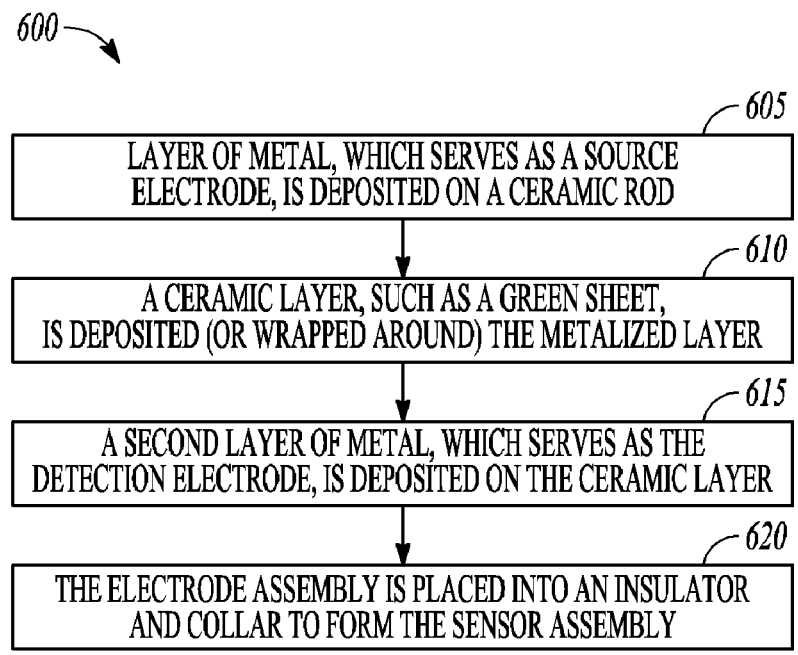
FIG. 6 is a flowchart of an example process to manufacture a particulate matter sensor.
Figure 7:
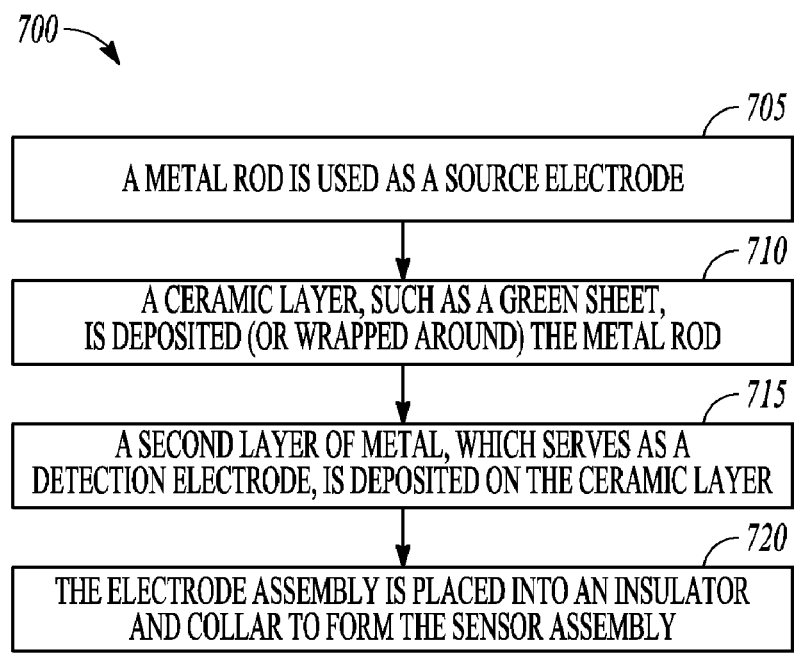
FIG. 7 is a flowchart of another example process to manufacture a particulate matter sensor.

FIGS. 6 and 7 are flowcharts of example processes 600 and 700 for manufacturing a particulate matter sensor. In general, the process 600 applies to the embodiment of FIG. 1, and the process 700 applies to the embodiment of FIG. 2. FIGS. 6 and 7 include a number of process blocks 605-620 and 705-720 respectively. Though arranged serially in the examples of FIGS. 6 and 7, other example embodiments may reorder the blocks, omit one or more blocks, and/or execute two or more blocks in parallel.

Referring to FIG. 6, at 605, a layer of metal, which serves as a source electrode, is deposited on a ceramic rod, and at 610, a ceramic layer, such as a green sheet, is deposited on (or wrapped around) the metalized layer. At 615, a second layer of metal, which serves as the detection electrode, is deposited on the ceramic layer. At 620, the electrode assembly is placed into an insulator and collar to form the sensor assembly. The insulator can be manufactured out of glass.

Referring to FIG. 7, at 705, a metal rod is used as a source electrode. At 710, a ceramic layer, such as a green sheet, is deposited on (or wrapped around) the metal rod. At 715, a second layer of metal, which serves as a detection electrode, is deposited on the ceramic layer. At 720, the electrode assembly is placed into an insulator and collar to form the sensor assembly. The insulator can be manufactured out of glass.

Thus, an example particulate matter sensor and process for the manufacture of a particulate matter sensor have been described. Although specific example embodiments have been described, it will be evident that various modifications and changes may be made to these embodiments without departing from the broader scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract is provided to comply with 37 C.F.R. §1.72(b) and will allow the reader to quickly ascertain the nature and gist of the technical disclosure. It is submitted with the understanding that it will not be used to interpret or limit the scope or meaning of the claims.

In the foregoing description of the embodiments, various features are grouped together in a single embodiment for the purpose of streamlining the disclosure. This method of disclosure is not to be interpreted as reflecting that the claimed embodiments have more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate example embodiment.

It should be understood that there exist implementations of other variations and modifications of the invention and its various aspects, as may be readily apparent, for example, to those of ordinary skill in the art, and that the invention is not limited by specific embodiments described herein. Features and embodiments described above may be combined with each other in different combinations. It is therefore contemplated to cover any and all modifications, variations, combinations or equivalents that fall within the scope of the present invention.

The invention claimed is:

1. A particulate matter sensor comprising:
   a ceramic rod;
   a first metal layer deposited on and surrounding the ceramic rod;
   a ceramic layer deposited on and surrounding the first metal layer; and
   a second metal layer deposited on and surrounding the ceramic layer;
   wherein the first metal layer serves as a source electrode; and
   wherein the second metal layer serves as a detection electrode.

2. The particulate matter sensor of claim 1, wherein the ceramic layer comprises a green ceramic sheet.

3. The particulate matter sensor of claim 1, wherein one or more of the ceramic rod, the first metal layer, the ceramic layer, and the second metal layer are co-fired.

4. The particulate matter senor of claim 1, wherein one or more of the ceramic rod and the ceramic layer comprise a low temperature co-fired ceramic or a high temperature co fired ceramic.

5. The particulate matter sensor of claim 1, comprising a housing configured for attachment to a diesel engine.

6. The particulate matter sensor of claim 5, wherein the particulate matter sensor is positioned after a diesel particulate filter.

7. The particulate matter sensor of claim 6, further comprising the diesel engine.

8. A particulate matter sensor comprising:
   a metal rod;
   a ceramic sheet deposited around the metal rod; and
   a metal layer deposited on and surrounding the ceramic sheet;
   wherein the metal rod serves as a source electrode; and
   wherein the metal layer serves as a detection electrode.

9. The particulate matter sensor of claim 8, wherein one or more of the metal rod, the ceramic sheet, and the metal layer are co-fired.

10. The particulate matter sensor of claim 8, comprising a housing configured for attachment to a diesel engine.

11. The particulate matter sensor of claim 10, wherein the particulate matter sensor is positioned after a diesel particulate filter.

12. The particulate matter sensor of claim 10, further comprising the diesel engine.

13. The particulate matter sensor of claim 8, wherein the ceramic sheet comprises a low temperature co-fired ceramic or a high temperature co-fired ceramic.

14. A process to manufacture a particulate matter sensor, the process comprising:
   depositing a first layer of metal onto a ceramic rod that the metal surrounds the ceramic rod:
   depositing a layer of ceramic onto the first layer of metal such that the ceramic layer surrounds the first layer of metal; and
   depositing a second layer of metal onto the layer of ceramic such that the second layer of metal surrounds the layer of ceramic.

15. The process of claim 14, comprising placing the ceramic rod, the first layer of metal, the layer of ceramic, and the second layer of metal into an insulator.

16. The process of claim 15, comprising attaching the particulate matter sensor to a diesel engine.

17. A process to manufacture a particulate matter sensor, the process comprising:

provi ding a metal rod;

depositing a ceramic layer on the metal rod such that the ceramic layer surrounds the metal rod; and depositing a metal layer on the ceramic layer such that the metal layer surrounds the ceramic layer.

18. The process of claim 17, comprising placing the metal rod, the ceramic layer, and the metal layer into an insulator.

* * * * *